United States Patent [19]
Belanger

[11] Patent Number: 5,125,927
[45] Date of Patent: Jun. 30, 1992

[54] BREAKAWAY ELECTRODE FOR SURGICAL CUTTING AND CAUTERIZING TOOL

[76] Inventor: Neil F. Belanger, 1117 St. Louis St., Edwardsville, Ill. 62025

[21] Appl. No.: 656,988

[22] Filed: Feb. 19, 1991

[51] Int. Cl.⁵ .............................................. A61B 17/39
[52] U.S. Cl. ........................................ 606/45; 606/49
[58] Field of Search ................ 606/29, 39, 45, 41, 606/49, 42; 219/69.15, 539, 542, 548–549; 338/203, 295, 319; 30/162, 351, 335

[56] References Cited

U.S. PATENT DOCUMENTS

| | | | |
|---|---|---|---|
| 3,448,518 | 6/1969 | Sklar | 30/162 |
| 4,063,356 | 12/1977 | Hepworth | 30/335 |
| 4,112,950 | 9/1978 | Pike | 606/42 |
| 4,427,006 | 1/1984 | Nottre | 606/42 |
| 4,655,215 | 4/1987 | Pike | 606/45 |

Primary Examiner—Lee S. Cohen
Assistant Examiner—Jeffrey R. Jastrzab
Attorney, Agent, or Firm—Rogers, Howell & Haferkamp

[57] ABSTRACT

A breakaway electrode for an electrosurgical cutting and cauterizing apparatus is provided that is comprised of several blade sections that are connected, end-to-end, in a longitudinal sequence. The sequential blade sections are interconnected by frangible connections that enable breaking away a used blade section at an end of the electrode and exposing a new blade section for use.

27 Claims, 2 Drawing Sheets

BREAKAWAY ELECTRODE FOR SURGICAL CUTTING AND CAUTERIZING TOOL

BACKGROUND OF THE INVENTION (1) Field of the Invention

The present invention relates to an electrode for use with an electrosurgical cutting and cauterizing instrument. In particular, the present invention relates to an electrosurgical cutting and cauterizing electrode that is comprised of several blade sections that are connected, end-to-end, in a longitudinal sequence. The sequential blade sections are interconnected by frangible connections that enable breaking away a used blade section at an end of the electrode and exposing a new blade section for use.

(2) Description of the Related Art

Electrosurgical instruments of the prior art that are used to both cut tissue and cauterize or coagulate open blood vessels commonly comprise a single electrode that is removably mounted in a scalpel handle. The scalpel handle is electrically connected by several conductors to a separate electrical power source. The scalpel handle conductors include a therapeutic current conductor between the handle and the power source, and two signal current conductors between the therapeutic current conductor in the handle and the power source. The two signal conductors complete two signal circuits to the power source that control the power source to produce a continuous sine wave signal for cutting purposes, or a pulsing signal for coagulating purposes. A grounding plate or pad on which a patient lays is connected by a further conductor to the power source.

The scalpel handle includes a socket for releasably receiving the prior art electrode. The socket is connected by the therapeutic current conductor to the separate power source. The prior art scalpel handle is also commonly provided with two separate manually actuated switches. The switches control connection of the electrode socket and the therapeutic current conductor to the two signal current conductors communicating the handle with the separate power source, and selectively control the supply of the continuous sine wave signal or the pulsing signal from the power source to the socket. By selectively actuating the two switches, the electrode inserted in the handle socket is subjected to either the continuous sine wave signal or the pulsing signal supplied to the socket by the separate power source. Electrosurgical instruments of this type are disclosed in U.S. Pat. No. 4,427,006, and U.S. Pat. No. 4,112,950.

Prior art electrodes are commonly configured from a flat strip of surgical steel. The electrodes are stamped from the strips in the configuration of a flat elongated member having beveled longitudinal edges that lead up to a rounded, blunt distal end. When subjected to the continuous current supplied by the separate power source, the beveled edges of the electrode are used in making incisions in tissue and cauterizing smaller blood vessels as incisions are made. When subjected to the second pulsing current supplied by the separate power source, the blunt, rounded end of the electrode is used in coagulating larger blood vessels.

Prior art electrodes have been found to be disadvantaged in that, after a relatively short period of use, blood begins to coagulate on the cutting edges and the blunt end of the electrode. Coagulation of blood on the electrode necessitates stopping surgery and cleaning the electrode several times during the course of one surgical operation, or stopping surgery so that the used electrode may be replaced with a new electrode. Both procedures require stopping surgery for a certain period of time while the electrode is cleaned or replaced.

SUMMARY OF THE INVENTION

The electrode of the invention is primarily intended for use with an electrosurgical cutting and cauterizing apparatus. However, the electrode may be used in other applications where the functions performed by the electrode are similar to those performed when used with an electrosurgical apparatus. The electrode is generally constructed of a plurality of substantially identical blade sections that are connected together, end-to-end, in a longitudinal sequence. Preferably, the electrode is manufactured from a thin strip of surgical steel.

The electrode is to be inserted into and releasably secured in a scalpel handle that, for the most part, functions in a similar manner to prior art handles. The scalpel handle, like prior art handles, is provided with electrical connections to a power source that include a therapeutic current conductor and two signal current conductors connected between the handle and the power source. The scalpel handle is provided with two separate manually actuated switches. Actuating a first of the two switches completes a circuit through the electrode conducting the first continuous sine wave signal supplied by the power source. Actuating the second switch completes a circuit through the electrode conducting the second pulsing signal supplied by the power source. Selective actuation of the first and second switches controls the power source to supply to the electrode projecting from the scalpel handle the desired mode of current for cutting or cauterizing purposes, respectively.

The scalpel handle used with the electrode of the present invention differs from prior art scalpel handles in that it is also provided with a manual actuator or other similar mechanism that engages with the electrode secured in the handle. The actuator causes the electrode to be incrementally advanced out of a forward end of the handle as the actuator is manually depressed. By depressing the manual actuator, the electrode is incrementally advanced out of the handle and sequential blade sections of the electrode project from the handle's forward end.

The electrode of the invention is generally a flat strip of surgical steel having several blade sections stamped into the strip. The individual blade sections stamped into the electrode are all connected together and are arranged end-to-end in a longitudinal sequence along the length of the electrode. In the preferred embodiment of the invention the electrode comprises four blade sections. However, the electrode may comprise as few as two blade sections or as many as five or more blade sections.

Each of the individual blade sections that make up the electrode are provided with a forward and rearward end. The forward end of the blade sections are provided with shoulders at their opposite lateral sides and a lancet tip that projects longitudinally forward from between the shoulders. The lancet tip is formed with opposite beveled edges that extend longitudinally forward from the shoulders, and a blunt rounded tip at the extreme distal end of the lancet tip. The opposite beveled edges and the rounded tip of the lancet tip are all cut completely through the electrode so that they may be separated from the next adjacent blade section stamped in the electrode without bending or deforming the lancet tip. The shoulders on opposite sides of the lancet tip are stamped into the electrode but are not cut completely through the electrode. Forming the shoulders in this manner provides a frangible connection between the shoulders of one blade section and the next adjacent blade of the electrode.

The rearward end of each blade section is formed with a pair of laterally spaced, longitudinally extending prongs and a slot formed between the prongs. The shape of the slot between the prongs is formed by, and the slot itself is occupied by, the lancet tip of the next adjacent blade section. Because the lancet tip of the next adjacent blade section is cut completely through the electrode, there is no connection between the rearwardly extending prongs of one blade section and the forwardly extending lancet tip of the adjacent blade section that extends between the prongs. At the rearward distal end of the spaced prongs of each blade section, the prongs are connected by a frangible connection to the shoulders at the forward end of the next adjacent blade section.

By stamping out each sequential blade section with the configuration described above, blade sections can be easily broken off from an end of the electrode without disturbing the lancet tip of the next adjacent blade section exposed by breaking off the preceding blade section.

Each of the sequential blade sections in the electrode are also provided with electrical contact surfaces for connection of the blade section to the separate power source. In the preferred embodiment of the invention, each blade section is provided with a therapeutic current connection and two contact surfaces for selectively connecting the blade section in two different electrical circuits conducting the two different signal currents produced by the electrical power source. Because the blade sections of the electrode are stamped out of a flat strip of surgical steel, the side surfaces of each blade section provide a smooth flat surface for engaging electrical contacts manipulated by the two switches of the scalpel handle to complete the two electrical circuits of different signal currents through the blade section. The electrical contacts with the electrode can be made anywhere along the length of the electrode.

In an alternate embodiment of the invention, each of the blade sections is comprised of a base member having a forward and rearward end and having a lancet tip projecting from the forward end of the base member. The lancet tip is again constructed of surgical steel. However, the base member in this embodiment of the invention is constructed of an insulating plastic capable of withstanding high temperatures. The base members mount and support the lancet tips of each blade section and expose a sufficient portion of the lancet tip to enable the electrical therapeutic current and signal current connections of a modified scalpel handle to be made with the lancet tip of each blade section.

The base members are also provided with cavities at their rearward ends. The cavities permit the insertion of a lancet tip and a portion of a base member of a next adjacent blade section into the cavity of the base member of the next forward blade section in the electrode's sequence of blade sections.

By providing the electrosurgical cutting and cauterizing electrode with a series of longitudinally sequenced blade sections, as the forward most blade section is soiled during use, the electrode may be easily advanced and the soiled blade section may be broken away from the frangible connections to expose the next adjacent blade section for use. This eliminates the problem of the time delay in surgery resulting from the need to repeatedly clean the prior art electrode or replace the electrode during its use.

BRIEF DESCRIPTION OF THE DRAWING FIGURES

Further objects and features of the present invention are revealed in the following detailed description of the preferred embodiment of the invention and in the drawing figures wherein.

DESCRIPTION OF THE PREFERRED EMBODIMENT

Figure 1:
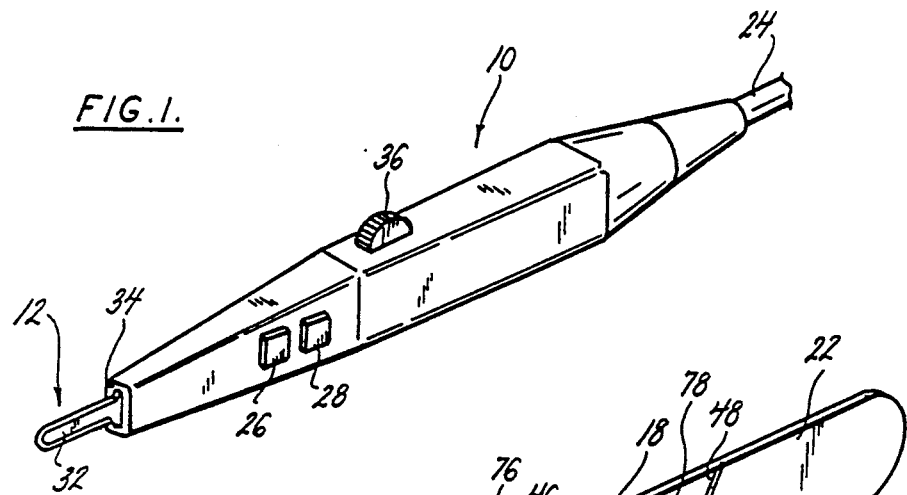
FIG. 1 is a perspective view of an electrosurgical scalpel handle that makes up the operative environment of the present invention.

In describing the best mode of the electrode of the invention, the electrode is described as being used with an electrosurgical cutting and cauterizing apparatus 10 such as that shown in FIG. 1 of the drawings. However, it should be understood that the operative environment of FIG. 1 is described for illustration purposes only and is not intended to be limiting. The electrode of the invention may be used in other applications and environments where the functioning of the electrode is similar to that of the electrode in the environment described with reference to FIG. 1.

Figure 2:
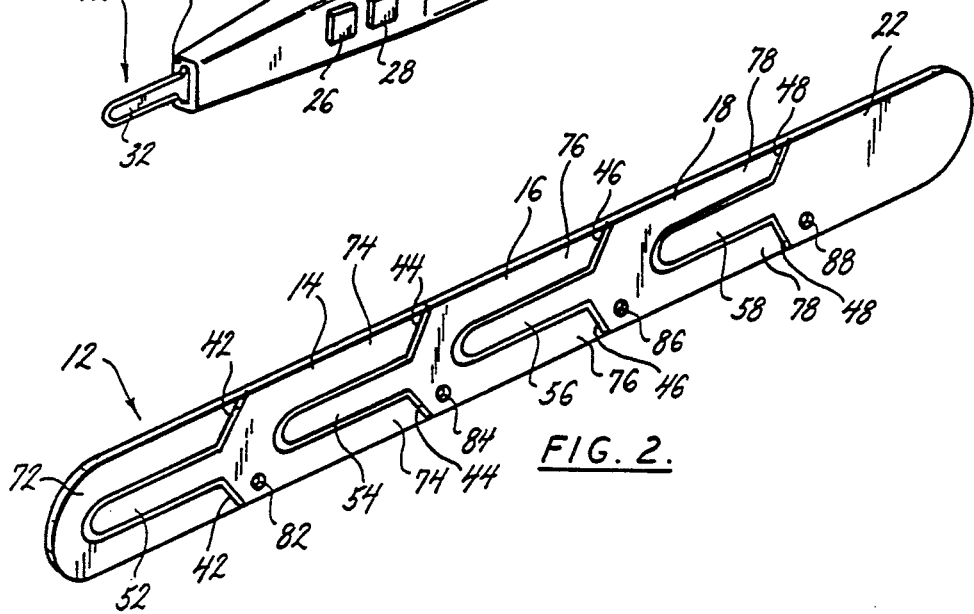
FIG. 2 is a perspective view of the electrosurgical electrode of the present invention.

The electrode of the invention is constructed from a thin strip of steel, preferably surgical steel. The electrode 12 is generally comprised of a plurality of substantially identical blade sections 14, 16, 18, 22 that are connected together in an end-to-end longitudinal sequence substantially as shown in FIG. 2.

The electrosurgical apparatus 10 or scalpel handle is designed to receive and securely hold the electrode 12 of the invention. The scalpel handle is not a part of the present invention and will not be described in great detail. The scalpel handle 10 functions in a manner similar to that of prior art scalpel handles such as those disclosed in U.S. Pat. No. 4,112,950 and U.S. Pat. No. 4,427,006. The scalpel handle 10 is provided with several electrical connections 24 to a separate power source (not shown). The electrical connections 24 provide a therapeutic current to the handle 10 and also supply two different signal currents to the handle from the separate electrical power source.

Two separate manually actuated switches 26, are provided on the exterior of the scalpel handle. Actuating the first 26 of the two switches completes an electrical circuit through the electrode 12 conducting a first continuous sine wave signal supplied by the power source (not shown]to the handle. Actuating the second switch 28 of the two switches completes an electrical circuit through the electrode 12 conducting a second pulsing signal supplied by the power source (not shown) to the handle. Selective actuation of the first and second switches 26, 28 supplies either the continuous sine wave signal or the pulsing signal to the tip of the electrode 32 projecting from the forward end 34 of the handle for cutting or coagulating purposes, respectively.

The modified scalpel handle 10 with which the electrode 12 of the invention is used differs from prior art scalpel handles in that it is also provided with a sealed manual actuator 36 on its exterior for advancing the electrode. The actuator 36 engages the electrode 12 in the interior of the handle 10. The engagement of the actuator 36 with the electrode 12 will cause the electrode to be advanced out of the forward end 34 of the handle as the actuator 36 is manually depressed. By depressing the manual actuator 36 downward, the electrode 12 is incrementally advanced out of the handle and sequential blade sections 14, 16, 18, 22 of the electrode project from the handle forward end.

As seen in FIG. 2, the electrode of the invention 12 is generally a flat strip with rounded ends having several blade sections 14, 16, 18, 22 stamped into the strip. The individual blade sections stamped into the electrode are all connected together and are arranged end-to-end in a longitudinal sequence along the length of the electrode. In FIG. 2, the electrode is shown comprising four blade sections 14, 16, 18, 22. However, it should be understood that the electrode may comprise as few as two blade sections or as many as five or more blade sections. The electrode shown in FIG. 2 comprising four blade sections is for illustrative purposes only.

Referring again to FIG. 2, each of the individual blade sections 14, 16, 18, 22 is provided with a forward end at the left hand side of the blade section, and a rearward end at the right hand side of the blade section. The forward ends of each of the individual blade sections 14, 16, 18, 22 are provided with shoulders 42, 44, 46, 48 at their opposite lateral sides, respectively. The forward ends of each of the individual blade sections 14, 16, 18, 22 are also provided with lancet tips 52, 54, 56, 58 that project longitudinally forward from between the respective shoulders 42, 44, 46, 48 of the blade sections.

Figure 3:
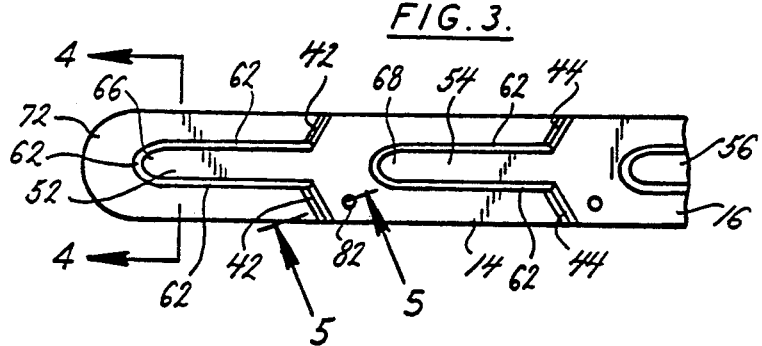
FIG. 3 is a segmented side view of the electrode of the present invention.
Figure 4:
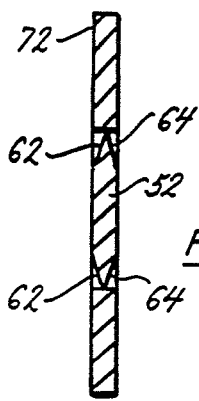
FIG. 4 is an end view in section of the electrode taken along the line 4—4 of FIG. 3.
Figure 5:
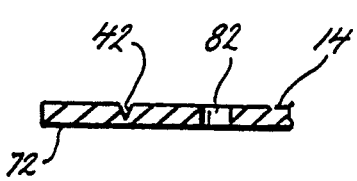
FIG. 5 is a segmented view in section of the electrode taken along the line 5—5 of FIG. 3.

Referring to FIGS. 3-5, each lancet tip is formed with opposite beveled edges 62, 64 that extend longitudinally forward from the shoulders 42, 44 of the blade sections 14, 16, respectively. A blunt rounded tip 66, 68 is formed at the extreme forward distal end of the lancet tips 52, 54 and the beveled edge 62, 64 of each lancet tip extends around the respective rounded tip end. The beveled edges along the opposite longitudinally extending sides and the rounded end of the lancet tips are all cut completely through the electrode as is shown in FIG. 4. The beveled edges of the lance tips cut through the electrode enable each of the lancet tips to be separated from the next adjacent blade section stamped in the electrode without bending or deforming the lancet tip.

Referring to FIG. 5, the shoulders 42 stamped in the electrode on opposite sides of the lancet tip 52 do not cut completely through the electrode. As is seen in FIG. 5, the groove cut into the electrode 12 to form the shoulder 42 leaves a thin portion of the electrode at the bottom of the groove that provides a frangible connection between the shoulders of the blade section and the next adjacent blade section of the electrode.

The shoulder 42 and frangible connection shown in FIG. 5 are between the forward most blade section 14 of the electrode 12 and a forward end portion 72 of the electrode that is broken away from the lancet tip 52 of the forward blade section 14 and discarded prior to use of the electrode. Although the forward end 72 of the electrode is not a blade section, the frangible connections connecting the forward end 72 to the shoulders 42 of the forward most blade section 14 are the same as the frangible connections provided at the shoulders 44, 46, 48 of the interconnected blade sections.

The rearward or right hand end of three blade sections 14, 16, 18 shown in drawing FIGS. 2 and 3 are formed with pairs of laterally spaced and longitudinally extending prongs 74, 76, 78, respectively. The rearward most blade section 22 is not provided with a rearwardly extending pair of prongs because the blade section is not connected to a further, rearward blade section. Each of the pair of prongs 74, 76, 78 is formed with a slot between the prongs. The slot between each pair of prongs 74, 76, 78 is shaped complimentary to the shape of the lancet tip 54, 56, 58 of the next rearwardly adjacent blade section 16, 18, 22, that extends into and fills the slot. Because the longitudinal beveled edges and rounded tips of the lancet tips 54, 56, 58 are cut completely through the electrode 12, there is no connection between the rearwardly extending pairs of prongs 74, 76, 78 of the blade sections 14, 16, 18 and the forwardly extending lancet tips 54, 56, 58 of the rearwardly adjacent blade sections 16, 18, 22 that extend between the prongs. The rearward most distal ends of the spaced prongs 74, 76, 78 of the blade sections 14, 16, 18 are connected by the previously described frangible connections to the shoulders 44, 46, 48 at the forward ends of the rearwardly adjacent blade sections 16, 18, 22, respectively.

By stamping out each of the sequential blade sections 14, 16, 18, 22 of the electrode 12 with the configuration described above, each blade sections can be easily broken off from its frangible connections to the next rearwardly adjacent blade section without disturbing the lancet tip of that blade section exposed by breaking off the preceding blade section.

By constructing the electrode from an elongate flat strip of material and stamping the sequential blade sections into the flat strip of material, each of the sequential blade sections in the electrode are provided with flat electrical contact surfaces on their opposite sides for connection of the blade sections to the separate power source. Because the electrode is a conductor, the electrical contacts to the electrode can be made at any point along either side of the electrode. In the preferred embodiment of the invention, each of the individual blade sections 14, 16, 18, 22 of the electrode are provided with holes 82, 84, 86, 88 extending through the respective blade sections. An extension of the manual actuator 36 engages in the holes and prevents the electrode from being pushed back into the handle 10 when the apparatus is in use. Pressing the manual actuator downward causes the extension to pull out of the hole it is engaged in, enabling one of the blade sections of the electrode to be pulled out of the front end 34 of the handle, and permitting the forward most blade section to be broken off. Releasing the actuator will cause it to engage in the next rearward hole of the electrode. The extension of the manual actuator may also be a conductor that provides the electrical connection between the therapeutic current conductor and the electrode as it engages in the hole of each blade section.

The sequential blade sections of the electrode 12 are selectively connected to the continuous sine wave signal conductor and the pulsing signal conductor of the electrical connections 24 between the handle 10 and the power source (not shown) by selective, manual actuation of the first and second switches 26, 28, respectively. By selective depression of the first and second switches 26, 28, the lancet tip 32 of the blade section projecting from the forward end 34 of the handle 10 is selectively connected in two different electrical circuits conducting the two different signal currents produced by the separate power source. Because the blade sections of the electrode are stamped out of a flat strip of conducting material, the opposite side surfaces of each blade section provide a smooth, flat surface for engaging electrical contacts (not shown) manipulated by the two switches of the scalpel handle 10 to complete the two electrical circuits of different signal currents through the blade section. In this manner, the lancet tip 32 projecting from the forward end 34 of the handle 10 is selectively supplied with the continuous sine wave signal for cutting purposes, or the pulsing signal for coagulating purposes.

Figure 6:
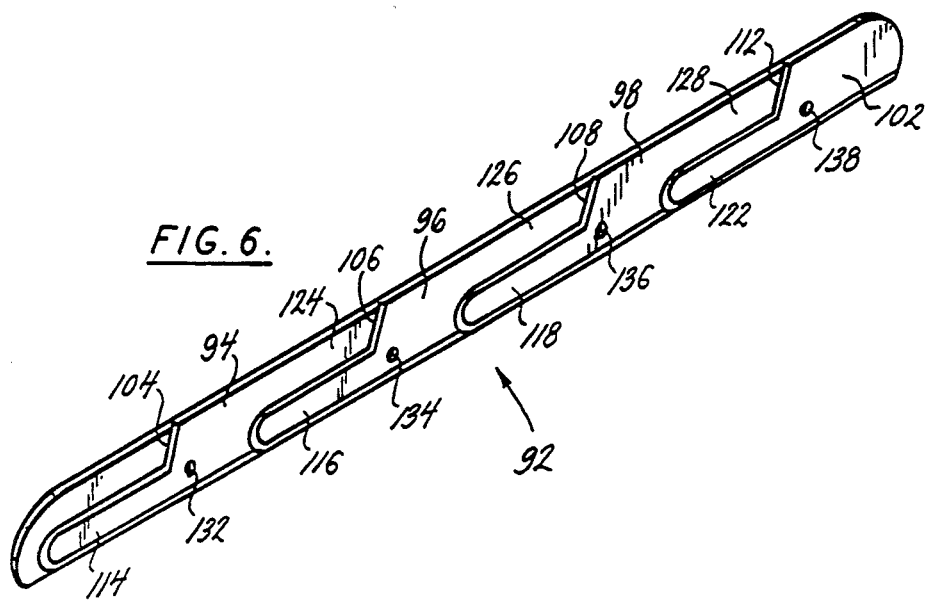
FIG. 6 is a side view of an alternate embodiment of the electrode of the invention.

An alternate embodiment of the electrode 92 is shown in FIG. 6 of the drawings. Like the electrode of the first embodiment, the electrode 92 of this embodiment is generally a flat strip with rounded ends having several blade sections 94, 96, 98, 102 stamped into the strip. The individual blade sections stamped into the electrode are all connected together and are arranged end-to-end in a longitudinal sequence along the length of the electrode. The electrode is shown in FIG. 6 as comprising four blade sections 94, 96, 98, 102. However, as in the first embodiment, it should be understood that the electrode may comprise as few as two blade sections or as many as five or more blade sections.

In this embodiment of the invention, the forward ends of each of the individual blade sections 94, 96, 98, 102 are provided with single shoulders 104, 106, 108, 112, respectively. The forward ends of each of the individual blade sections 94, 96, 98, 102 are also provided with lancet tips 114, 116, 118, 122, respectively. Each of the lancet tips project longitudinally forward from its adjacent shoulder. The shoulders stamped in the electrode adjacent the lancet tips do not cut completely through the electrode. As in the first embodiment, a groove cut into the electrode 92 to form each of the individual shoulders 104, 106, 108, 112 leaves a thin portion of the electrode at the bottom of the groove that provides a frangible connection between the shoulders of each of the blade sections and the next adjacent blade sections of the electrode.

The rearward end of the three forward blade sections 94, 96, 98 are formed with longitudinally extending prongs 124, 126, 128 and slots provided laterally adjacent the prongs. The shape of the slot adjacent each prong is formed by, and the slot itself is occupied by, the lancet tip of the next adjacent blade section. Because the lancet tip of the next adjacent blade section is cut completely through the electrode, there is no connection between the rearwardly extending prong of one blade section and the forwardly extending lancet tip of the adjacent blade section. At the rearward distal end of the prongs 124, 26, 128 of the forward three blade sections, the prongs are connected by the frangible connections to the shoulders 106, 108, 112 at the forward ends of the rearwardly adjacent blade sections.

Like the first embodiment of the invention, by stamping out each sequential blade section with the configuration described above, a blade section can be easily broken off from a forward end of the electrode without disturbing the lancet tip of the next adjacent blade section exposed by breaking off the preceding blade section.

Each of the sequential blade sections in the electrode shown in FIG. 6 are also provided with the holes 132, 134, 136, 138 and the electrical contact surfaces as described in the first embodiment of the invention for connection of the blade sections to the separate power source. This embodiment of the electrode of the invention functions in substantially the same manner as the previously described embodiment of the electrode of the invention.

Figure 7:
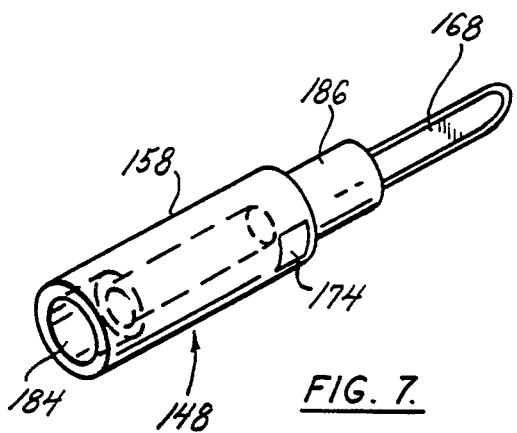
FIG. 7 is a perspective view of a blade section of an additional alternate embodiment of the invention; and, FIG. 8 is a side view of an electrode comprising the blade section embodiment of FIG. 7.
Figure 8:
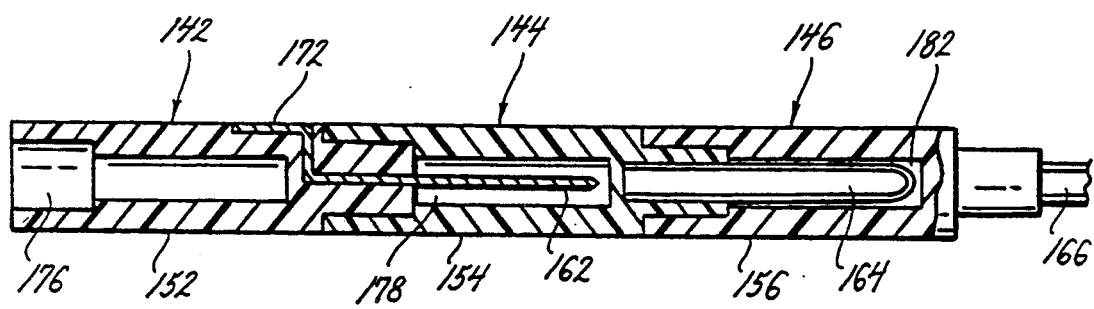

In a further alternate embodiment of the invention shown in FIGS. 7 and 8, each of the blade sections 142, 144, 146, 148 is comprised of a base member 152, 154, 156, 158 having a forward, rightward end and a rearward, leftward end as viewed in FIGS. 7 and 8. A lancet tip 162, 164, 166, 168 projects from the forward ends of the respective base members. The lancet tips are preferably constructed of surgical steel. However, the base member in this embodiment of the invention is preferably constructed of an insulating plastic capable of withstanding high temperatures. The base members mount and support the lancet tips of each blade section and expose a sufficient portion (as seen at 172 and 174) of the lancet tips to enable the electrical therapeutic current and signal current connections of a modified scalpel handle to be made with the lancet tip of each blade section.

As seen in FIGS. 7 and 8, the base members 152, 154, 156, 158 are also provided with cavities 176, 178, 182, 184 at their rearward ends. The cavities permit the insertion of a lancet tip and a portion of a base member of a rearward adjacent blade section into the cavity of the base member of the next forward blade section in the electrode's sequence of blade sections. Referring to FIG. 7, the insertion of a forward portion 186 of a rearward base member into the cavity of a forward base member provides the connection between adjacent base members that make up one electrode. The base members of adjacent blade sections may also be provided with frangible connections to hold the blade sections together until it is desired to break away a used blade section. This embodiment of the electrode of the invention functions in substantially the same manner as the previously described embodiments of the electrode of the invention.

While the present invention has been described by reference to specific embodiments, it should be understood that modifications and variations of the invention may be constructed without departing from the scope of the invention defined in the following claims.

What is claimed is:

1. An electrosurgical electrode comprising:
   a plurality of like blade sections connected together, end-to-end, in a longitudinal sequence, each blade section of the plurality having a first and a second end;

the first end of at least one blade section being connected by a frangible connection to the second end of an adjacent blade section;

the second end of at least one blade section having a longitudinally projecting tip for electrosurgically cutting tissue and cauterizing tissue; and, at least one blade section having an electrical contact that is selectively connected to a source of electric power to enable the electrode to perform electrosurgical cutting and cauterizing operations.

2. The electrode of claim 1, wherein:

the second end of at least one blade section has a lancet tip that is separated from a first end of an adjacent blade section, the lancet tip having a beveled cutting edge and a rounded cauterizing edge.

3. The electrode of claim 2, wherein:

the second end of the one blade section has a shoulder adjacent the lancet tip, the shoulder being connected by a frangible connection to a first end of an adjacent blade section.

4. The electrode of claim 3, wherein:

the shoulder and the lancet tip are formed integrally from a single piece of material.

5. The electrode of claim 3, wherein:

the at least one blade section has a base member having first and second ends, the first end of the base member corresponding to the first end of the blade section and the second end of the base member corresponding to the shoulder of the blade section, the base member being connected to and supporting the lancet tip of the blade section.

6. The electrode of claim 5, wherein:

the lancet tip of at least one blade section is inserted into and seats inside the base member of an adjacent blade section.

7. The electrode of claim 5, wherein:

the base member is not electrically conductive.

8. The electrode of claim 2, wherein:

the second end of the one blade section has shoulders on opposite lateral sides of the lancet tip, the shoulders being connected by frangible connections to a first end of an adjacent blade section.

9. The electrode of claim 1, wherein:

the first end of at least one blade section of the plurality of blade sections is formed with a longitudinally extending prong and a slot adjacent the prong, and the second end of the blade section is formed with a longitudinally extending lancet tip and a shoulder adjacent the tip.

10. The electrode of claim 9, wherein:

the prong of the one blade section is connected by a frangible connection to a shoulder of an adjacent blade section and a lancet tip of the adjacent blade section extends into the slot of the one blade section.

11. The electrode of claim 9, wherein:

the shoulder of the one blade section is connected by a frangible connection to a prong of an adjacent blade section and a lancet tip of the one blade section extends into a slot of the adjacent blade section.

12. The electrode of claim 1, wherein:

the first end of at least one blade section of the plurality of blade sections is formed with a pair of longitudinally extending prongs and a slot between the prongs, and the second end of the blade section is formed with a longitudinally extending lancet tip and a pair of shoulders on opposite sides of the tip.

13. The electrode of claim 12, wherein:

the pair of prongs of the one blade section are connected by a frangible connection to a pair of shoulders of an adjacent blade section and a lancet tip of the adjacent blade section extends into the slot of the one blade section.

14. The electrode of claim 12, wherein:

the pair of shoulders of the one blade section are connected by a frangible connection to a pair of prongs of an adjacent blade section and the lancet tip of the one blade section extends into a slot between a pair of prongs of an adjacent blade section.

15. The electrode of claim 1, wherein:

each blade section of the plurality of blade sections is provided with a first electrical contact connectable to a first source of current, and each blade section is provided with a second electrical contact selectively connectable to a second source of 16. The electrode of claim 15, wherein:

each blade section of the plurality of blade sections is provided with a third electrical contact selectively connectable to a third source of current.

17. An electrode for use with an electrosurgical cutting and cauterizing tool, the electrode comprising:

a plurality of like blade sections connected together, end-to-end, in a longitudinal sequence, each blade section of the plurality having first and second ends;

the first end of at least one blade section being connected by a frangible connection to the second end of an adjacent blade section;

the second end of at least one blade section having a lancet tip projecting longitudinally from the second end; and, each blade section having a first electrical contact connectable to a first source of current, and having a second electrical contact selectively connectable to a second source of current.

18. The electrode of claim 17, wherein:

each blade section of the plurality of blade sections is provided with a third electrical contact selectively connectable to a third source of current.

19. The electrode of claim 17, wherein:

the second end of the one blade section is connected by a frangible connection to a first end of an adjacent blade section, the frangible connection being adjacent the lancet tip of the one blade section and the lancet tip extending longitudinally beyond the frangible connection.

20. An electrosurigcal apparatus comprising:

an electrode having a plurality of like blade sections connected together, end-to-end, in a longitudinal sequence, each blade section of the plurality having first and second ends;

the first end of at least one blade section being connected by a frangible connection to the second end of an adjacent blade section;

the second end of at least one blade section having a lancet tip projecting longitudinally from the second end;

each blade section having a first electrical contact connectable to a first source of current, and having a second electrical contact selectively connectable to a second source of current; and an electrosurgical cutting and cauterizing tool, the plurality of like blade sections being received in the electrosurgical cutting and cauterizing tool, a manual actuator is provided on the tool and sequential blade sections of the plurality of like blade sections are advance out of the electrosurgical cutting and cauterizing tool by manual manipulation of the manual actuator of the tool.

21. An electrode for use with an electrosurgical cutting and cauterizing tool, the electrode comprising:

a plurality of like blade sections connected together, end-to-end, in a longitudinal sequence, each blade section of the plurality having a first and a second end;

the first end of at least one blade section being connected by a frangible connection to the second end of an adjacent blade section;

the second end of at least one blade section having a beveled edge for cutting tissue and a rounded edge for cauterizing tissue; and, at least one blade section having an electrical contact that is selectively connected to a source of electric power to heat the one blade section.

22. An electrosurgical apparatus comprising:

a plurality of like blade sections connected together, end-to-end, in a longitudinal sequence, each blade section of the plurality having a first and second end;

the first end of at least one blade section being connected by a frangible connection to the second and of an adjacent blade section;

the second end of at least one blade section having a beveled edge for cutting tissue and a rounded edge for cauterizing tissue;

at least one blade section having an electrical contact that is selectively connected to a source of electric power to heat the one blade section; and an electrosurgical cutting and cauterizing tool, the plurality of like blade sections being received in the electrosurgical cutting and cauterizing tool, a manual actuator is provided on the tool and sequential blade sections of the plurality of like blade sections are advance out of the electrosurgical cutting and cauterizing tool by manual manipulation of the manual actuator of the tool.

23. An electrosurgical apparatus comprising:

an electrode having a plurality of like blade sections connected together, end-to-end, in a longitudinal sequence, each blade section of the plurality having a fist and a second end;

the first end of at least one blade section being connected by a frangible connection to the second end of an adjacent blade section;

the second end of at least one blade section having a tip for electrosurgically cutting tissue and cauterizing tissue;

at least one blade section having an electrical contact that is selectively connected to a source of electric power to enable the electrode to perform electrosurgical cutting and cauterizing operations; and an electrosurgical cutting and cauterizing instrument, the plurality of like blade sections being received in the electrosurgical cutting and cauterizing instrument, a manual actuator is provided on the instrument and sequential blade sections of the plurality of like blade sections are advanced out of the electrosurgical cutting and cauterizing instrument by manual manipulation of the manual actuator of the instrument.

24. In an electrosurgical electrode for use with an electrosurgical cutting and cauterizing instrument, the improvement comprising:

a plurality of electrode sections, each electrode section of the plurality having a first and a second end; and, means for connecting the first end of at least one electrode section to the second end of another of the electrode sections by a frangible connection.

25. The electrode of claim 24, wherein:

the plurality of electrode sections are all connected together, end-to-end, in a longitudinal sequence.

26. The electrode of claim 24, wherein:

each electrode section has a first electrical contact connectable to a first source of electric power, a second electrical contact selectively connectable with a second source of electric power, and a third electrical contact selectively connectable to a third source of electric power.

27. The electrode of claim 24, wherein:

the second end of the one electrode section has a lancet tip projecting longitudinally from the second end, and the lancet tip extends longitudinally beyond the means for connecting the first end of the one electrode section to the second end of the other electrode section.

* * * * *